United States Patent
Johnson (10) Patent No.: US 8,100,883 B1
(45) Date of Patent: Jan. 24, 2012

(54) RIGHT-SIDE CORONARY SINUS LEAD DELIVERY CATHETER

(75) Inventor: Eric T. Johnson, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1957 days.

(21) Appl. No.: 10/916,148

(22) Filed: Aug. 11, 2004

(51) Int. Cl.
*A61M 25/00* (2006.01)

(52) U.S. Cl. ........................ 604/532; 604/523

(58) Field of Classification Search ............... 604/507, 604/508, 510, 264, 523–525, 528, 530, 532; 607/122, 125
See application file for complete search history.

(56) References Cited

U.S. PATENT DOCUMENTS

| | | | |
|---|---|---|---|
| 5,203,776 A | 4/1993 | Durfee | |
| 5,322,509 A | 6/1994 | Rickerd | |
| 5,423,772 A | 6/1995 | Lurie et al. | |
| 5,549,581 A | 8/1996 | Lurie et al. | |
| 5,603,704 A | 2/1997 | Brin et al. | |
| 5,643,231 A | 7/1997 | Lurie et al. | |
| 5,722,963 A | 3/1998 | Lurie et al. | |
| 5,846,229 A * | 12/1998 | Berg | 604/528 |
| 5,873,842 A | 2/1999 | Brennen et al. | |
| 5,876,385 A | 3/1999 | Ikari et al. | |
| 5,879,499 A | 3/1999 | Corvi | |
| 5,971,974 A | 10/1999 | Keisz | |
| 5,984,909 A | 11/1999 | Lurie et al. | |
| 6,001,085 A | 12/1999 | Lurie et al. | |
| 6,126,649 A | 10/2000 | VanTassel et al. | |
| 6,132,417 A | 10/2000 | Kiesz | |
| 6,277,107 B1 | 8/2001 | Lurie et al. | |
| 6,445,958 B1 | 9/2002 | Machek et al. | |
| 6,458,107 B1 | 10/2002 | Ockuly | |
| 6,610,058 B2 | 8/2003 | Flores | |
| 6,612,999 B2 | 9/2003 | Brennan et al. | |
| 6,638,268 B2 * | 10/2003 | Niazi | 604/528 |
| 6,656,166 B2 | 12/2003 | Lurie et al. | |
| 6,723,083 B2 | 4/2004 | Kiemeneij | |
| 6,758,854 B1 | 7/2004 | Butler et al. | |
| 6,823,217 B2 | 11/2004 | Rutten et al. | |
| 7,041,097 B1 * | 5/2006 | Webler | 606/41 |
| 2003/0028153 A1 | 2/2003 | Brennan et al. | |
| 2003/0040736 A1 * | 2/2003 | Stevens et al. | 604/532 |
| 2003/0144657 A1 * | 7/2003 | Bowe et al. | 606/41 |
| 2003/0195525 A1 | 10/2003 | Peterson et al. | |
| 2003/0208141 A1 | 11/2003 | Worley et al. | |

(Continued)

OTHER PUBLICATIONS

Pressure Products Booklet from May 2002 NASPE Conference, 2 pp.

*Primary Examiner* — Kevin C Sirmons
*Assistant Examiner* — Laura Schell
(74) *Attorney, Agent, or Firm* — Faegre & Benson LLP (57) ABSTRACT

A catheter for insertion into the right atrium from the right subclavian vein has an elongate flexible shaft having a proximal portion and a distal portion. The distal portion has a preformed shape including a first arc portion having a curvature of from about 20 degrees to about 50 degrees relative to the proximal portion and a second arc portion extending distally from the first arc and having a curvature of from about 135 to about 200 degrees relative to the first portion. The first arc has an arc radius of from about 6 inches to about 10 inches and the second arc has an arc radius of from about 1 to about 2 inches. The catheter terminates in a generally straight terminal portion extending distally from the preformed shape.

10 Claims, 6 Drawing Sheets

U.S. PATENT DOCUMENTS

| | | |
|---|---|---|
| 2003/0208220 A1 | 11/2003 | Worley et al. |
| 2004/0019359 A1* | 1/2004 | Worley et al. ............ 606/129 |
| 2004/0092844 A1 | 5/2004 | Johnson et al. |
| 2004/0102830 A1 | 5/2004 | Williams |
| 2004/0116993 A1 | 6/2004 | Clemens et al. |
| 2004/0220520 A1 | 11/2004 | Simpson et al. |

* cited by examiner

RIGHT-SIDE CORONARY SINUS LEAD DELIVERY CATHETER

CROSS-REFERENCE TO RELATED APPLICATION(S)

This application is related to co-pending, commonly-assigned U.S. patent application Ser. No. 10/916,148, entitled "CORONARY SINUS LEAD DELIVERY CATHETER," filed on even date herewith, which is incorporated herein by reference.

TECHNICAL FIELD

This invention relates to cardiovascular guide catheters and methods of using the catheters. More specifically, it relates to a guide catheter for locating and cannulating the coronary sinus.

BACKGROUND

Guiding catheters are instruments that allow a physician to access and cannulate vessels in a patient's heart for conducting various medical procedures, including venography and implantation of cardiac pacing devices. Cannulating heart vessels requires navigating a small-diameter flexible guide catheter through the tortuous vasculature into a heart chamber, and then into a destination heart vessel. Once the destination heart vessel is reached, the catheter acts as a conduit for insertion of payloads, for example pacing leads, into the vessel.

Guiding catheter systems are often configured with a pre-shaped profile that is optimized for the intended vessel destination. One commonly accessed destination vessel for placement of the cardiac pacing leads is the coronary sinus. Typically, access to the coronary sinus is gained through the left subclavian vein. The coronary sinus may also be accessed through the right subclavian vein.

There is a need for a lead delivery system and method to allow accurate and rapid lead implantation and anchoring in the coronary sinus entering the right atrium from the right side.

SUMMARY

According to one embodiment, the present invention is a catheter for accessing the coronary sinus from a right-side insertion. The catheter includes an elongate flexible shaft having a proximal portion and a distal portion. A first segment of the distal portion of the shaft is preformed with a curvature of from about 20 to about 50 degrees relative to the proximal portion and has a first arc radius of from about 6 to about 10 inches. A second segment of the distal portion of the shaft extends distally adjacent the first segment and is preformed with a curvature of from about 135 to about 200 degrees relative to the first segment and has an arc radius of from about 1 to about 2 inches. The second segment curves opposite the first segment, forming the distal portion into a general S-shape adapted for insertion into one of the right subclavian vein, the right brachiocephalic vein, the right cephalic, the right internal jugular vein or the right external jugular vein. In one embodiment, the first segment has an arc length of from about 3 to about 8 inches and the second segment has an arc length of from about 3 to about 6 inches. According to another embodiment, the first segment has a curvature of about 30 degrees and an arc radius of about 7.96 inches and the second segment has a curvature of about 169.4 degrees and an arc radius of about 1.42 inches.

According to another embodiment, the present invention is method of cannulating the coronary sinus of the heart from a right side insertion. The method includes providing a catheter having a flexible elongate shaft with a proximal portion and a distal portion. A first segment of the distal portion is preformed with a curvature of from about 20 to about 50 degrees relative to the proximal portion and has a first arc radius of from about 6 to about 10 inches and a second segment of the distal portion extending distally adjacent the first segment is preformed with a curvature of from about 135 to 200 degrees relative to the first segment and has a second arc radius of from about 1 to about 2 inches. The second segment curves opposite the first segment, forming the shaft into a general S-shape. The distal portion is inserted into one of the right subclavian vein, the right brachiocephalic vein, the right cephalic vein, the right internal jugular vein or the right external jugular vein. The proximal portion is manipulated so as to insert the distal portion into the coronary sinus. According to one embodiment, manipulating the proximal portion further includes advancing the distal portion into the superior vena cava, then into the distal portion into the right atrium using the superior vena cava for support until the distal portion crosses the tricuspid valve. The distal portion is torqued 90 degrees counterclockwise to maneuver the distal portion into the same plane as the coronary sinus ostium. The distal portion is withdrawn back into the right atrium while maintaining torque. The distal portion is advanced into the coronary sinus ostium while maintaining torque.

According to another embodiment, the present invention is a method of cannulating the coronary sinus of the heart from a right side insertion. The method includes providing a catheter having an elongate flexible shaft with a proximal portion and a distal portion. A first segment of the distal portion of the shaft is preformed with a curvature of from about 90 degrees to about 150 degrees relative to the proximal portion and an arc radius of from about 1 to about 1.5 inches. The distal portion is inserted into one of the right subclavian vein, the right brachiocephalic vein, the right cephalic vein, the right internal jugular vein or the right external jugular vein. The proximal portion is manipulated so as to insert the distal portion into the coronary sinus.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
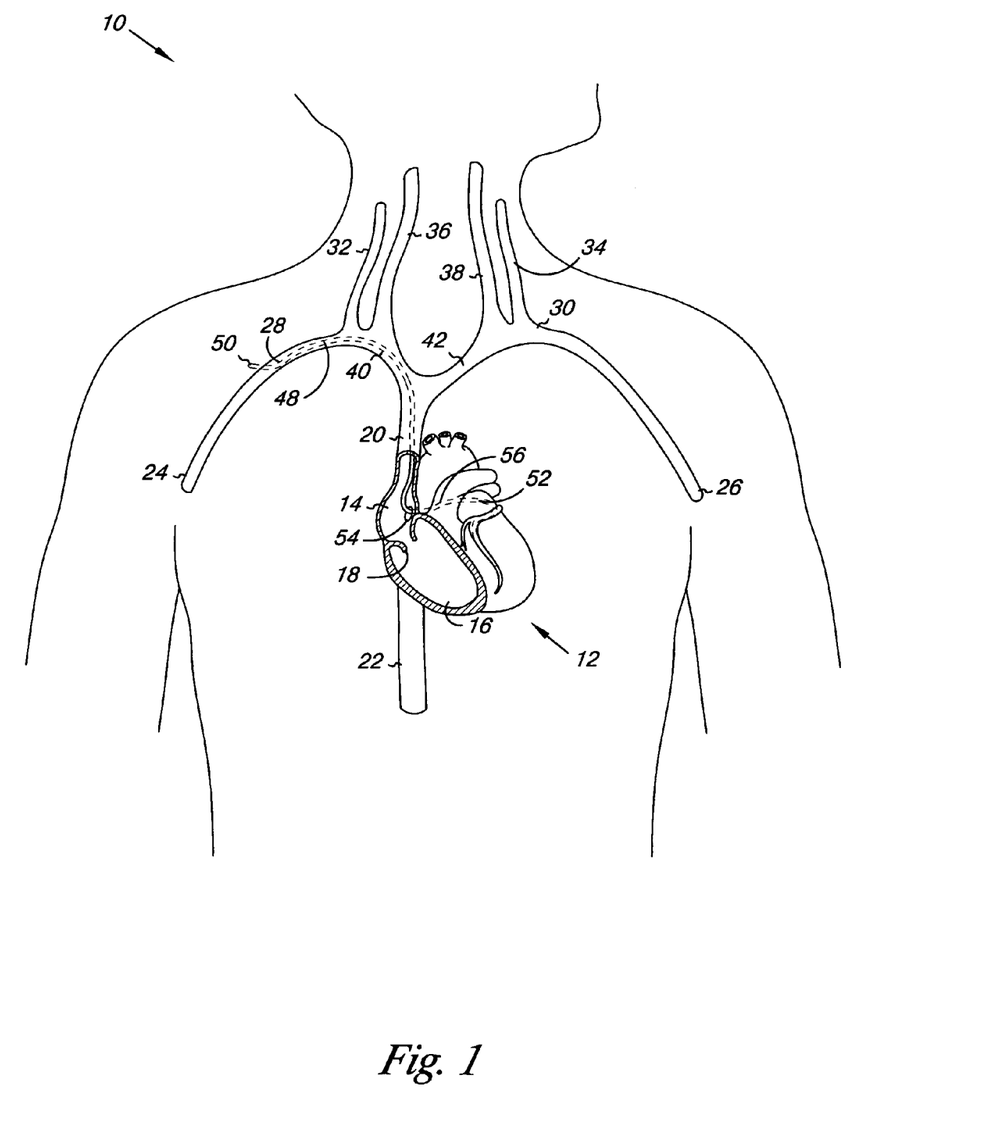
FIG. 1 is a schematic view of a catheter deployed in a heart and parts of the vascular system, according to one embodiment of the present invention.

FIG. 1 shows a catheter 10 deployed in a human heart 12 according to one embodiment of the present invention. As shown in FIG. 1, the heart 12 includes a right atrium 14 and a right ventricle 16 separated by a tricuspid valve 18. During normal operation of the heart 12, deoxygenated blood is fed into the right atrium 14 through the superior vena cava 20 and the inferior vena cava 22. The major veins supplying blood to the superior vena cava 20 include the right and left axillary veins 24 and 26, which flow into the right and left subclavian veins 28 and 30. The right and left external jugular 32 and 34, along with the right and left internal jugular 36 and 38, join the right and left subclavian veins 28 and 30 to form the right and left brachiocephalic veins 40 and 42. The right and left brachiocephalic veins 40 and 42 combine to flow into the superior vena cava 20.

The catheter 10, shown in FIG. 1, includes a flexible, elongate shaft 48 extending from a proximal portion 50 to a distal portion 52. As shown in FIG. 1, the catheter 10 enters the vascular system through a wall of the right subclavian vein 28, extends through the right brachiocephalic vein 40 and the superior vena cava 20, and enters the right atrium 14. As further shown, catheter 10 then enters the coronary sinus ostium 54 so that the distal portion 52 of the catheter 10 is located in the coronary sinus 56. In other embodiments of the present invention, the catheter 10 enters the vascular system through the right axillary vein 24, the right external jugular 32, the right internal jugular 36, or the right brachiocephalic vein 40. The catheter 10 may be a guide catheter for assisting with placement of a cardiac pacing lead.

Figure 2:
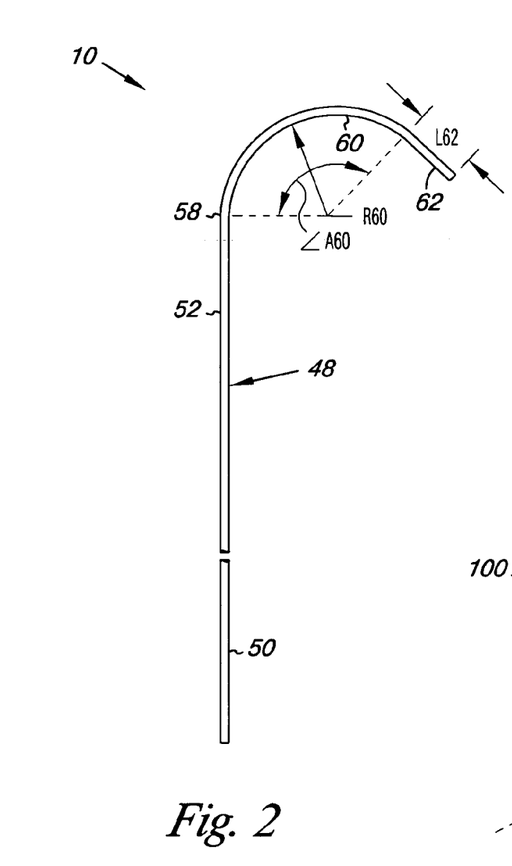
FIG. 2 is a side view of a catheter according to one embodiment of the present invention.

FIG. 2 illustrates features of the catheter 10 in accordance with one embodiment of the present invention. The catheter 10 includes a flexible elongate shaft 48 having a proximal portion 50 and a distal portion 52. The proximal portion 50 is manipulated by the surgeon to insert the distal portion 52 into the patient's anatomy and access the coronary sinus 56. The proximal portion 50 is generally straight. The distal portion 52, however, is advantageously pre-shaped beginning at a deflection location 58, providing an optimized geometry for locating specific vascular features (e.g., the coronary sinus 56).

As shown in FIG. 2, the distal portion 52 includes a first arc or catheter segment 60. In one embodiment, the catheter segment 60 extends through an arc A60 of from about 40 to about 160 degrees relative to the proximal portion 50. In another embodiment, the catheter segment 60 extends through an arc A60 of from about 90 to about 150 degrees relative to the proximal portion 50. In one embodiment, the catheter segment 60 extends through an arc A60 of about 135 degrees relative to the proximal portion 50. In one embodiment, the catheter segment 60 has a co-planar configuration such that the pre-formed shape lies in a plane.

To provide the overall shape, the catheter segment 60 has a specific radius R60. In various embodiments, the present example is scaled up or down to allow for different sized patient physiology. In one embodiment, the catheter segment 60 is curved so as to have an arc radius R60 of from about 0.5 to about 2 inches. In another embodiment, the catheter segment 60 is curved so as to have an arc radius R60 of from about 1 inch to about 1.5 inches. In another embodiment, the catheter segment 60 is curved so as to have an arc radius R60 of about 1.19 inches.

The distal portion 52 terminates in a generally straight end portion 62. According to one embodiment, the end portion 62 has a length L62 of from about 0.1 to about 2.5 inches. According to another embodiment, the length L62 of the end portion 62 is from about 0.3 to about 1 inch. According to yet another embodiment, the length L62 of the end portion 62 is about 0.56 inches.

It will be appreciated by those skilled in the art that the pre-formed curve allows the distal portion 52 to be steered by rotating the proximal portion 50. The ability to rotationally steer the distal portion 52 provides a guide catheter 10 according to the present embodiment useful in locating specific vascular features. In particular, the configuration of the pre-formed curve enables the guide catheter 10 to find support from the walls of the superior vena cava 20, rather than the right atrium 14, during right side insertion procedures. This is important because the size, configuration and location of the right atrium 14 tends to vary widely from patient to patient, particularly in patients having diseases of the heart. In contrast, the superior vena cava 20 tends to remain relatively constant in size and location, such that less time need generally be spent on locating the coronary sinus ostium 54.

The shaft 48 of the catheter 10 may be made from any material generally known in the art, including for example PEBAX® and urethane. In one example, the catheter 10 is formed by melting PEBAX® under a shrink tube, stripping the shrink tube, installing a shape mandrel and heating it to a forming temperature. In one embodiment, a pre-shaped wire or stylet is inserted into a lumen in the mandrel to give the mandrel the desired shape. The catheter 10 is then placed over the mandrel and heated to allow it to take the desired shape. In one embodiment, for example, the catheter 10 is heated at about 280° Fahrenheit for about 20 minutes. Upon cooling the catheter 10 will retain the shape of the mandrel. An alternate construction includes a multi-layer design. In one embodiment, the shaft 48 includes a support material such as steel braiding, for example.

The distal portion 52 also includes a series of sections having different lengths. These sections are made of a thermoplastic material such as a thermo polymer having a varying durometer or degree of hardness. According to one embodiment, the hardness of the distal portion 52 softens proximally to distally, such that the distal portion 52 has a lower degree of hardness than the proximal portion 50. In one embodiment, any thermoplastic material is used to form the catheter 10.

Figure 3:
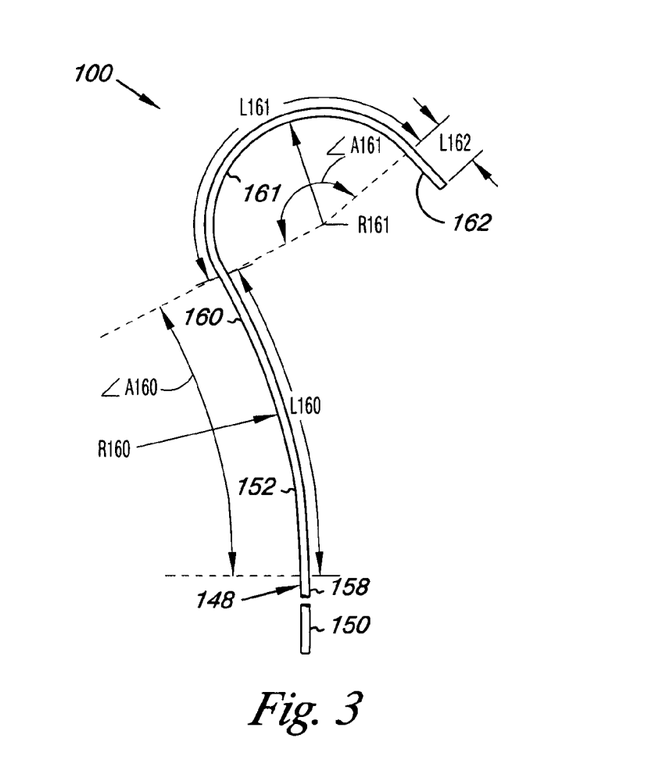
FIG. 3 is a side view of a catheter according to another embodiment of the present invention.

FIG. 3 shows a catheter 100 having a flexible, elongate shaft 148 in accordance with another embodiment of the present invention. The catheter 100 has a proximal portion 150 and a distal portion 152. The proximal portion 150 is substantially straight. The distal portion 152, however, is advantageously pre-shaped beginning at a deflection location 158. The pre-shaped distal portion 152 includes a first arc or catheter segment 160 and a second arc or catheter segment 161 extending distally from the first segment 160. The first segment 160 is formed with a curvature generally opposite that of the second segment 161, so that the distal portion 152 of catheter 100 has a generally S-shaped configuration. The first segment 160, in cooperation with the second segment 161, provides an optimized geometry for locating specific vascular features (e.g., the coronary sinus 56). In one embodiment, the catheter segment 160 extends through an arc A160 of from about 5 to about 80 degrees relative to the proximal portion 50 and the catheter segment 161 extends through an arc A161 of from about 5 to about 225 degrees relative to the first segment 160. In another embodiment, the catheter segment 160 extends through an arc A160 of from about 20 to about 50 degrees relative to the proximal portion 50 and the catheter segment 161 extends through an arc A161 of from about 135 to about 200 degrees relative to the first segment 160. According to another embodiment, the catheter segment 160 extends through an arc A160 of about 30 degrees relative to the proximal portion 150 and the catheter segment 161 extends through an arc A161 of about 169.4 degrees relative to the catheter segment 160. In one embodiment, the curved segments 160 and 161 have a co-planar configuration such that the pre-formed shape lies in a plane.

To provide the overall shape, the catheter segments 160, 161 have specific arc radii R160 and R161, respectively. In various embodiments, the present example can be scaled up or down to allow for different sized patient physiology. In one embodiment, the catheter segment 160 is curved so as to have an arc radius R160 of from about 4 inches to about 13 inches and the catheter segment 161 is curved so as to have an arc radius R161 of from about 0.5 inches to about 3.0 inches. In another embodiment, the arc radius R160 of segment 160 is from about 6 to about 10 inches and the arc radius R161 of segment 161 is from about 1 to about 2 inches. In yet another embodiment, the catheter segment 160 is curved so as to have an arc radius R160 of about 7.96 inches and the catheter segment 161 is curved so as to have an arc radius R161 of about 1.42 inches.

In various embodiments, the catheter segments 160 and 161 have different arc lengths. In one embodiment, the catheter segment 160 has an arc length L160 of from about 0.5 inches to about 13 inches and the catheter segment 161 has an arc length L161 of from about 0.5 inches to about 9 inches. In another embodiment, the arc length L160 of the catheter segment 160 is from about 3 inches to about 8 inches and the arc length L161 of the catheter segment 161 is from about 3 inches to about 6 inches. In yet another embodiment, the arc length L160 of catheter segment 160 is about 4.06 inches and the arc length L161 of catheter segment 161 is about 4.19 inches.

The distal portion 152 terminates in a generally straight end portion 162. According to one embodiment, the end portion 162 has a length L162 of from about 0.1 to about 3.5 inches. In other embodiments, the catheter 100 does not include the end portion 162.

The shaft 148 of the catheter 100 may be made from any material generally known in the art, as described with reference to FIG. 2A above.

Typically, access to the coronary sinus 56 is gained through the left subclavian 30, or other left side access vessels. Less frequently, for various reasons, it is necessary or desirable to access the coronary sinus 56 through the right subclavian 28, as shown in FIG. 1, or other right side access vessels. As shown in FIG. 1, the contours of the left side and right side vessels differ. Because a left side insertion is more common, most surgical techniques for accessing the coronary sinus 56 are adapted to accommodate the contours of the left side vessels. A second surgical technique adapted for the right side vessel contours is usually employed for right side insertions. A catheter according to the present invention, however, is advantageously adapted to be deployed for right side insertion in accordance with well-known left side insertion techniques, described in further detail below. A single surgical technique for both left and right side insertions reduces surgical time and mistakes caused by practicing unfamiliar right side insertion techniques.

Figures 4A, 4B:
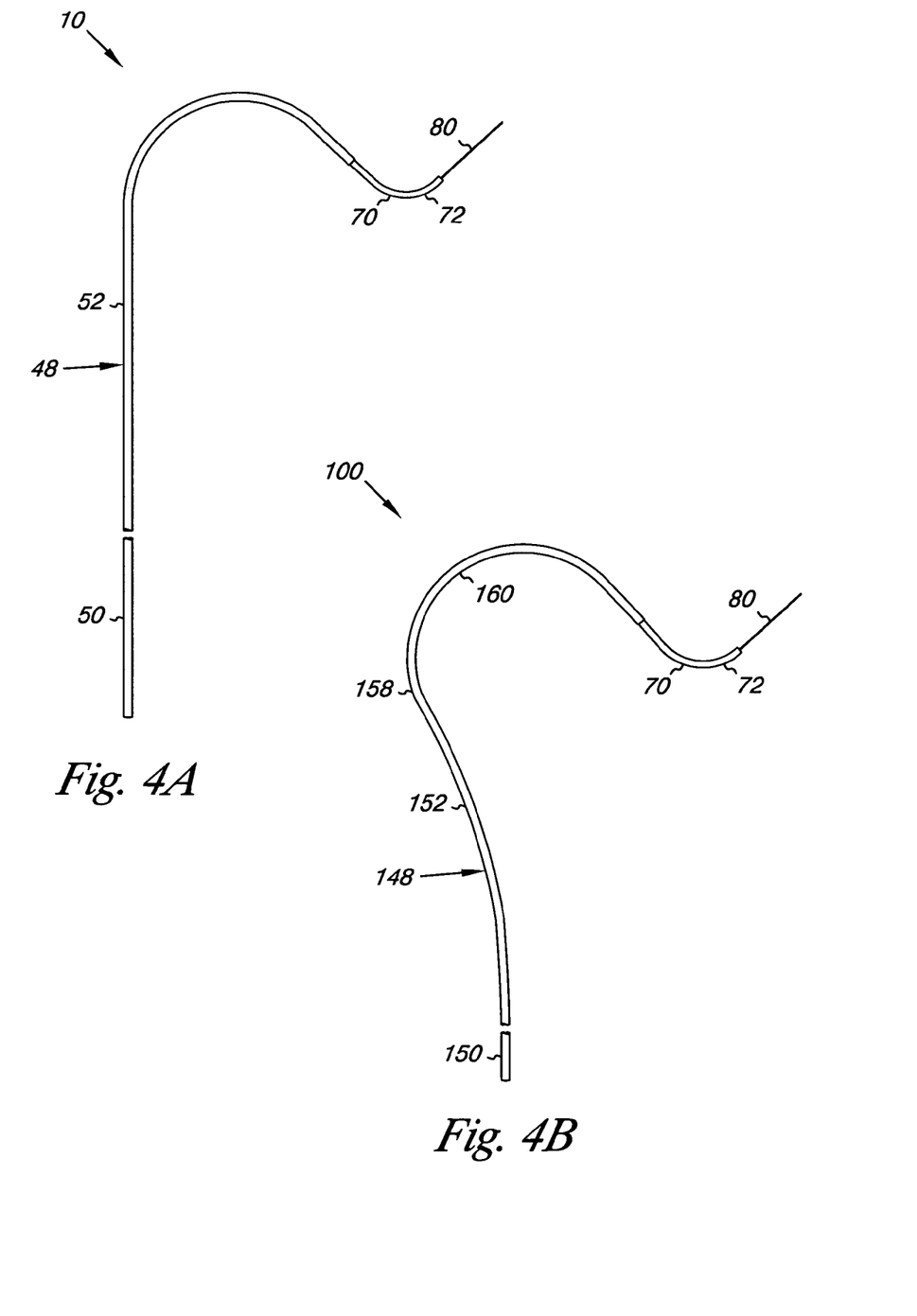
FIG. 4A is a side view of a catheter assembly according to one embodiment of the present invention.
FIG. 4B is a side view of a catheter assembly according to another embodiment of the present invention.

FIGS. 4A and 4B show the guide catheters 10 and 100 of FIGS. 2 and 3, respectively, assembled with an inner catheter 70. Referring generally to FIG. 4B, the inner catheter 70 has a preformed distal end 72, so that relative rotation and extension of the inner catheter 70 and guide catheter 100 provides the distal end 152 of the guide catheter 100 with an adjustable range of two- and three dimensional shapes. An example of this is described is U.S. Patent Publication 2003/0144657, which is hereby incorporated by reference. Furthermore, as illustrated, extension of the distal end 72 of the inner catheter 70 beyond the distal end 152 of the guide catheter shaft 148 results in a catheter assembly having a compound curvature.

Figure 5:
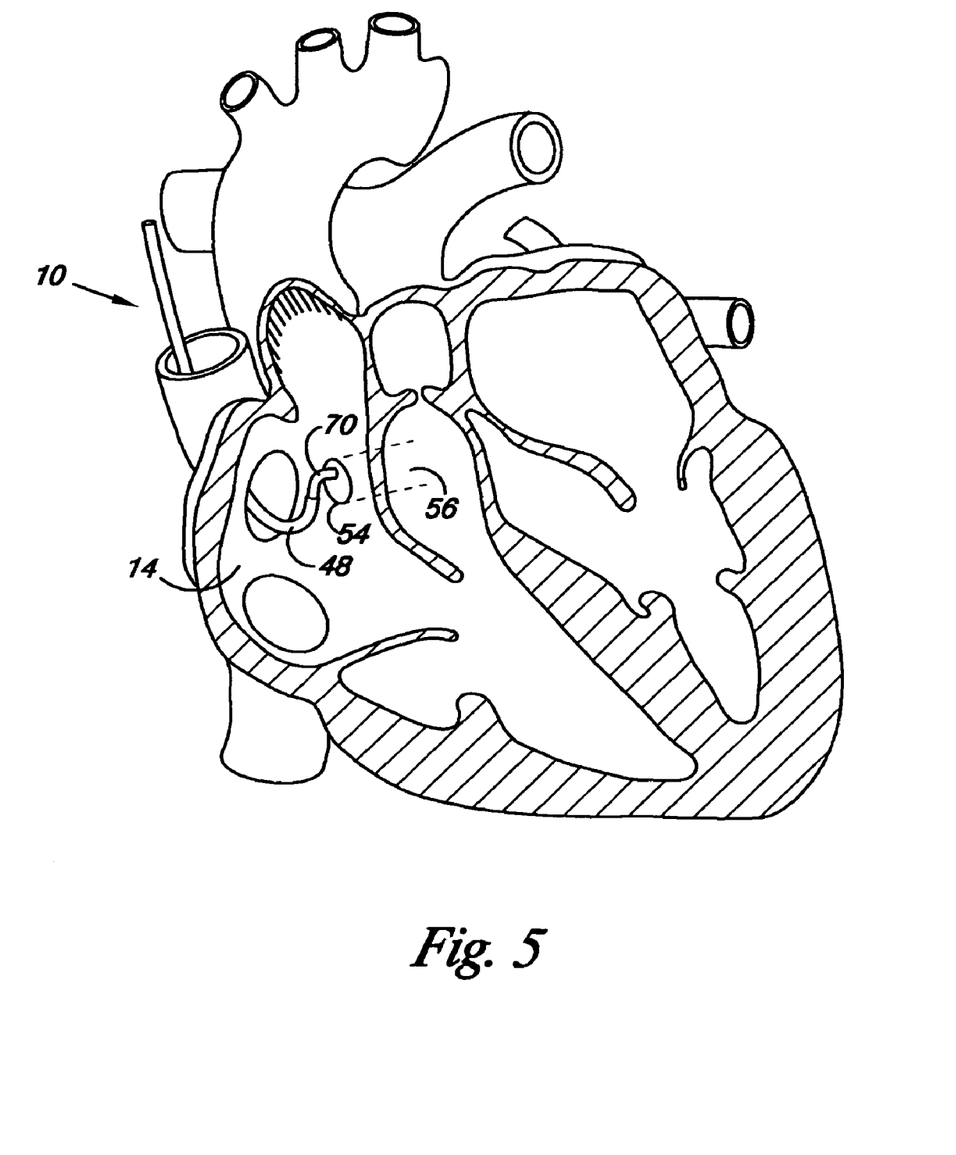
FIG. 5 is a schematic view of the catheter assembly of FIG. 4B deployed in a heart according to one embodiment of the present invention.

FIG. 5 shows the catheter assembly of FIG. 4B deployed in the heart 12. The compound curvature of the catheter assembly 100 provides easy access through the coronary sinus ostium 54 from the right atrium 14. The inner catheter 70 is advanced through the guide catheter shaft 148 and longitudinally extended to sub-select a branch of the coronary sinus 56. The guide catheter 100 is then advanced over the inner catheter 70 into the side branch. The inner catheter 70 is removed by proximally sliding the inner catheter 70 out of the catheter 100.

Optionally, a guide wire 80 may also be employed in conjunction with a guide catheter according to the present invention (See FIGS. 4A and 4B). The guide wire 80 is often introduced through the access vessel into the right atrium 14. The guide catheter 100 is advanced over the guide wire 80 into the right atrium 14 through the superior vena cava 20, for example. Typically, the catheter 100 is then deployed over the guide wire 80, the guide wire 80 helping to provide support and guidance for the catheter assembly 100 as it is advanced into the right atrium 14. From the right atrium 14, the catheter 100 is used to effectively locate and cannulate the coronary sinus 56.

After the guide catheter shaft 148 is seated in the coronary sinus 56, the guide catheter shaft 148 can be used to introduce a payload into the heart 12. If the guide wire 80 or inner catheter 70 were used, they may also be removed. The payload in one exemplary embodiment is a pacing lead. Once the payload has been successful seated, the guide catheter 100 can then be removed. Assuming the payload is to remain in the heart, the guide catheter 100 is moved in a proximal direction over the payload until the guide catheter 100 is removed from the access vessel.

Figure 6:
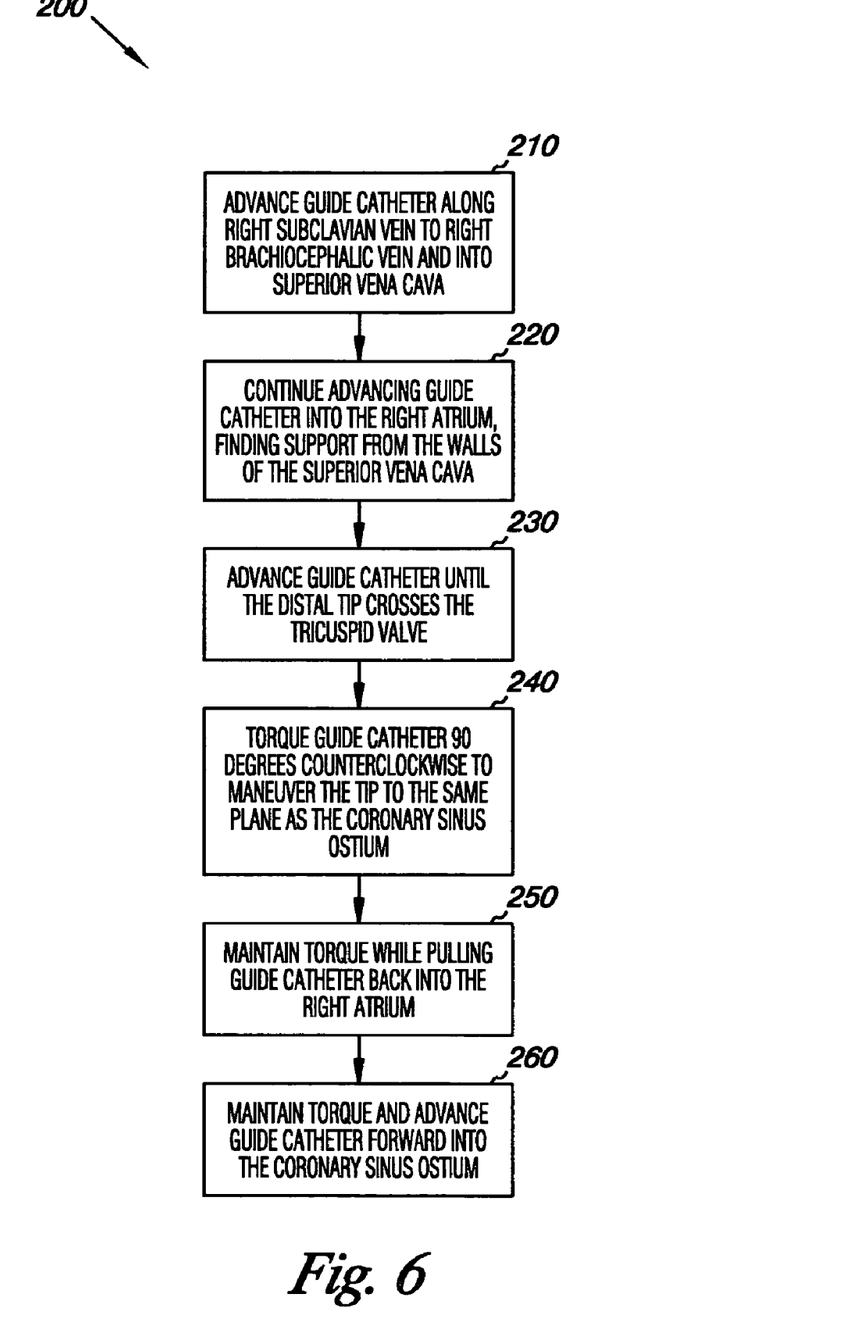
FIG. 6 is a flow chart depicting a method of accessing the coronary sinus according to one embodiment of the present invention.

FIG. 6 illustrates one embodiment of a method 200 of employing a guide catheter of the present invention. A guide catheter in accordance with the present invention is advanced into the superior vena cava from the right subclavian vein (block 210). The guide catheter is advanced into the right atrium, using the walls of the superior vena cava for support (block 220). The guide catheter is advanced until the distal tip crosses the tricuspid valve (block 230). The guide catheter is torqued 90 degrees counterclockwise to maneuver the distal tip into the same plane as the coronary sinus ostium (block 240). The torque is maintained while pulling the guide catheter back into the right atrium (block 250). Finally, torque is maintained and the guide is advanced forward through the coronary sinus ostium (block 260).

Figure 7:
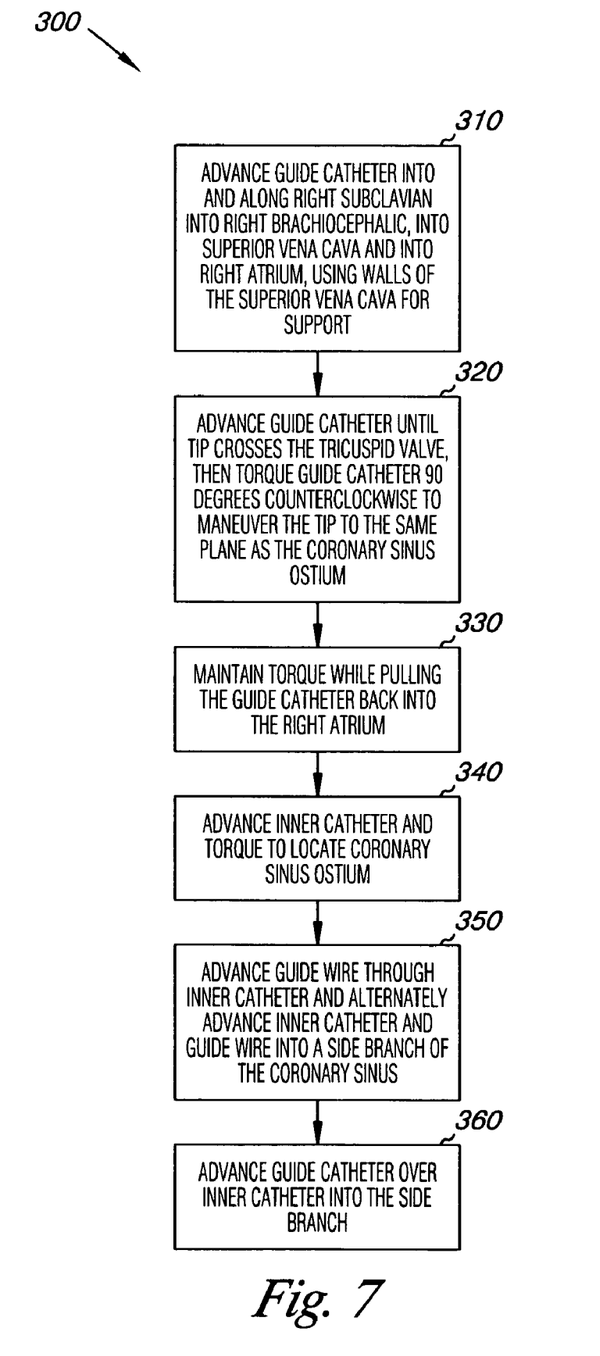
FIG. 7 is a flow chart depicting a method of accessing the coronary sinus according to another embodiment of the present invention.

FIG. 7 illustrates another method 300 of employing a guide catheter in accordance with the present invention in conjunction with an inner catheter and a guide wire. The guide catheter is advanced into the superior vena cava from the right subclavian vein and into the right atrium, using the walls of the superior vena cava for support (block 310). The guide catheter is advanced until the tip crosses the tricuspid valve, then torqued 90 degrees counterclockwise to maneuver the tip into the same plane as the coronary sinus ostium (block 320). Torque is maintained while pulling the guide catheter back into the right atrium (block 330). An inner catheter is advanced through the guide catheter and torqued to locate the coronary sinus ostium (block 340). A guide wire is advanced through the inner catheter and the inner catheter and guide wire are alternately advanced through the coronary sinus ostium and into a side branch of the coronary sinus (block 350). Finally, the guide catheter is advanced over the inner catheter into the side branch of the coronary sinus (block 360).

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

I claim:

1. A method of cannulating the coronary sinus of the heart from a right side insertion, the method comprising:
    selecting a catheter having an elongate flexible shaft with a proximal portion and a distal portion, the distal portion of the shaft preformed with a proximal curved segment extending distally from the proximal portion of the shaft having a curvature of from about 20 to about 50 degrees relative to the proximal portion of the shaft and an arc radius of from about 6 to about 10 inches, a distal curved segment extending distally from the proximal curved segment and having a curvature of from about 135 degrees to about 200 degrees relative to the proximal curved segment and an arc radius of from about 1 to about 2 inches, and a substantially straight terminal segment extending distally from the distal curved segment and having a length of from about 0.1 to about 3.5 inches, the distal curved segment being curved in a direction opposite the curvature of the proximal curved segment;
    inserting the distal portion into one of the right subclavian vein, the right brachiocephalic vein, the right cephalic vein, the right internal jugular vein or the right external jugular vein; and
    manipulating the proximal portion so as to insert the distal portion into the coronary sinus, including:
    advancing the distal portion into the superior vena cava;
    advancing the distal portion into the right atrium using the superior vena cava for support until the distal portion crosses the tricuspid valve;
    torquing the distal portion 90 degrees counterclockwise after crossing the tricuspid valve to maneuver the distal portion into the same plane as the coronary sinus ostium;
    withdrawing the distal portion back into the right atrium while maintaining torque; and
    advancing the distal portion into the coronary sinus ostium while maintaining torque.

2. The method of claim 1, further including providing the distal curved segment with a curvature of about 135 degrees relative to the proximal curved segment and an arc radius of about 1.42 inches.

3. The method of claim 1, further including providing the terminal segment with a length of about 3.5 inches.

4. The method of claim 1 wherein the proximal curved segment has a curvature of about 30 degrees relative to the proximal portion, and the distal curved segment has a curvature of about 169.4 degrees relative to the proximal curved segment and an arc length of about 4.19 inches.

5. The method of claim 1 wherein the proximal curved segment has an arc length of from about 3 to about 8 inches and the distal curved segment has an arc length of from about 3 to about 6 inches.

6. The method of claim 5 wherein the proximal curved segment has an arc length of about 4.06 inches and the distal curved segment has an arc length of about 4.19 inches.

7. The catheter of claim 1 wherein the proximal curved segment has a curvature of about 30 degrees relative to the proximal portion and an arc radius of about 7.96 inches and the distal curved segment has a curvature of about 169.4 degrees relative to the proximal curved segment and an arc radius of about 1.42 inches.

8. A method of cannulating the coronary sinus of the heart from a right side insertion, the method comprising:
    selecting a catheter having an elongate flexible shaft with a proximal portion and a distal portion, the distal portion of the shaft preformed with a proximal curved segment extending distally from the proximal portion of the shaft having a curvature of from about 20 to about 50 degrees relative to the proximal portion of the shaft and an arc radius of from about 6 to about 10 inches, a distal curved segment extending distally from the proximal curved segment and having a curvature of from about 135 degrees to about 200 degrees relative to the proximal curved segment, and an arc radius of from about 1 to about 2 inches, and a substantially straight terminal segment extending distally from the distal curved segment and having a length of from about 0.1 to about 3.5 inches, the distal curved segment being curved in a direction opposite the curvature of the proximal curved segment;
    inserting the distal portion into one of the right subclavian vein, the right brachiocephalic vein, the right cephalic vein, the right internal jugular vein or the right external jugular vein; and
    advancing the distal portion through the superior vena cava into the right atrium and across the tricuspid valve, and subsequently advancing the distal portion into the coronary sinus while applying and maintaining counterclockwise torque on the distal portion.

9. The method of claim 8 wherein the proximal curved segment has an arc length of from about 3 to about 8 inches and the distal curved segment has an arc length of from about 3 to about 6 inches.

10. The method of claim 9 wherein the proximal curved segment has an arc length of about 4.06 inches and the distal curved segment has an arc length of about 4.19 inches.

* * * * *